(12) United States Patent
Carlson et al.

(10) Patent No.: US 7,213,743 B2
(45) Date of Patent: May 8, 2007

(54) SYSTEM AND METHODS FOR SUPERMARKET SHOPPING LIST ELECTIONS BASED ON GOALS

(75) Inventors: Michael P. Carlson, Austin, TX (US); Linda A. Lisle, Cedar Park, TX (US); Herman Rodriguez, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 14 days.

(21) Appl. No.: 11/111,527

(22) Filed: Apr. 21, 2005

(65) Prior Publication Data

US 2006/0237523 A1  Oct. 26, 2006

(51) Int. Cl.
G06F 17/00 (2006.01)
G06Q 10/00 (2006.01)

(52) U.S. Cl. .......................... 235/375; 705/2
(58) Field of Classification Search ............... 235/375, 235/383; 705/2
See application file for complete search history.

(56) References Cited

U.S. PATENT DOCUMENTS

| | | | |
|---|---|---|---|
| 5,884,281 A | 3/1999 | Smith et al. | 705/26 |
| 6,024,281 A * | 2/2000 | Shepley | 235/375 |
| 6,026,376 A | 2/2000 | Kenney | 705/27 |
| 6,513,017 B1 | 1/2003 | Howard et al. | 705/28 |
| 6,820,062 B1 | 11/2004 | Gupta et al. | 705/16 |
| 6,872,077 B2 * | 3/2005 | Yeager | 434/127 |
| 2002/0047867 A1 * | 4/2002 | Mault et al. | 345/810 |
| 2003/0171944 A1 | 9/2003 | Fine et al. | 705/1 |
| 2003/0208110 A1 * | 11/2003 | Mault et al. | 600/300 |
| 2004/0026503 A1 | 2/2004 | Gantz | 235/383 |
| 2005/0049920 A1 | 3/2005 | Day et al. | 705/15 |

* cited by examiner

Primary Examiner—Thien M. Le
Assistant Examiner—April A. Taylor
(74) Attorney, Agent, or Firm—Scott Charles Richardson; McGrath, Geissler Olds & Richardson, PLLC

(57) ABSTRACT

Methods 300 and systems 100 for evaluating proposed food purchases which vary from a pre-planned diet are provided. A nutrition-related scheme, the pre-planned diet, is developed on the basis of achieving a primary goal such as increasing the intake of a particular nutrient or losing a certain amount of weight. The nutrition-related scheme, which may be stored in a memory 103 of a computer 120, includes a list of approved food items. When a user proposes to substitute a food item for an approved food item a version of the program stored on a PDA 120 determines whether the substituted item negatively interacts with any of the approved diet items, for example, affecting the user's ability to metabolize a nutrient in the approved item.

19 Claims, 3 Drawing Sheets

SYSTEM AND METHODS FOR SUPERMARKET SHOPPING LIST ELECTIONS BASED ON GOALS

BACKGROUND

1. Field

The present embodiments relate generally to systems and methods for shopping, and more specifically to systems and methods for evaluating the impact of proposed food purchases on a pre-planned diet.

2. Background

People have good intentions when it comes to setting goals related to their health and personal well being. Each new year we set New Year's resolutions to lose weight, eat healthier, exercise more, or other equally well-intentioned goals. More often than not these goals for the new year soon fall by the wayside as lost causes, only to be taken up again the following year. Many systems and methods have been devised in an effort to improve the chances of achieving one's goals, especially diet-related goals.

Published U.S. Patent Application 2005/0049920 to Day et al. describes a system for tracking the nutritional content of food purchases. Day et al's system monitors purchases a consumer is contemplating and suggests an alternative purchase which is appropriate to the consumer's diet. U.S. Pat. No. 5,836,312, issued to Moore discusses a system of dieting which takes into account the physiological parameters of a person, for example, age, height, weight and build of the person. Records are kept to account for food consumed by the dieter. If necessary, the system suggests changes to the person's diet after considering the caloric intake and physiological parameters of the person. Another conventional system described in U.S. Pat. No. 6,249,773 entails the creation of supermarket shopping lists based on the shopping history of a particular shopper. Similarly, the convention system of Canadian CA 1996002193869 creates a shopping list based on properties of the shopper or the shopper's family, the previous purchase history and household size.

One problem with these conventional systems is that they do not take into account the effect of the interaction between the present diet food items with an item substituted by the dieter.

SUMMARY

Embodiments disclosed herein address the above stated needs by considering the impact of substituting an approved diet food item with a substitute item. In various embodiments the proposed substitute item is evaluated to determine whether it has a negative impact-on any of the approved items. The negative impact may occur due to the substitute item interacting with one of the approved diet items, affecting the body's ability to metabolize the approved diet item.

Some embodiments are drawn to methods and systems for evaluating proposed food purchases which include the storing of a nutrition-related scheme based on achieving a primary goal. The primary goal may be to alter the intake of a particular nutrient, or to lose a certain amount of weight, or other such goal. The nutrition-related scheme typically includes a list of approved food items that the user may purchase. If the user proposes to purchase an item which is not part of the list of approved food items, the system makes a determination of whether the proposed substitute item would negatively interact with any of the approved food items. The system communicates this determination to the user, for example, by displaying a message on a computer or personal digital assistant (PDA) screen.

BRIEF DESCRIPTION OF THE DRAWINGS

The accompanying drawings, which are incorporated in and constitute part of the specification, illustrate various embodiments of the invention. Together with the general description, the drawings serve to explain the principles of the invention. In the drawings.

DETAILED DESCRIPTION

Figure 1:
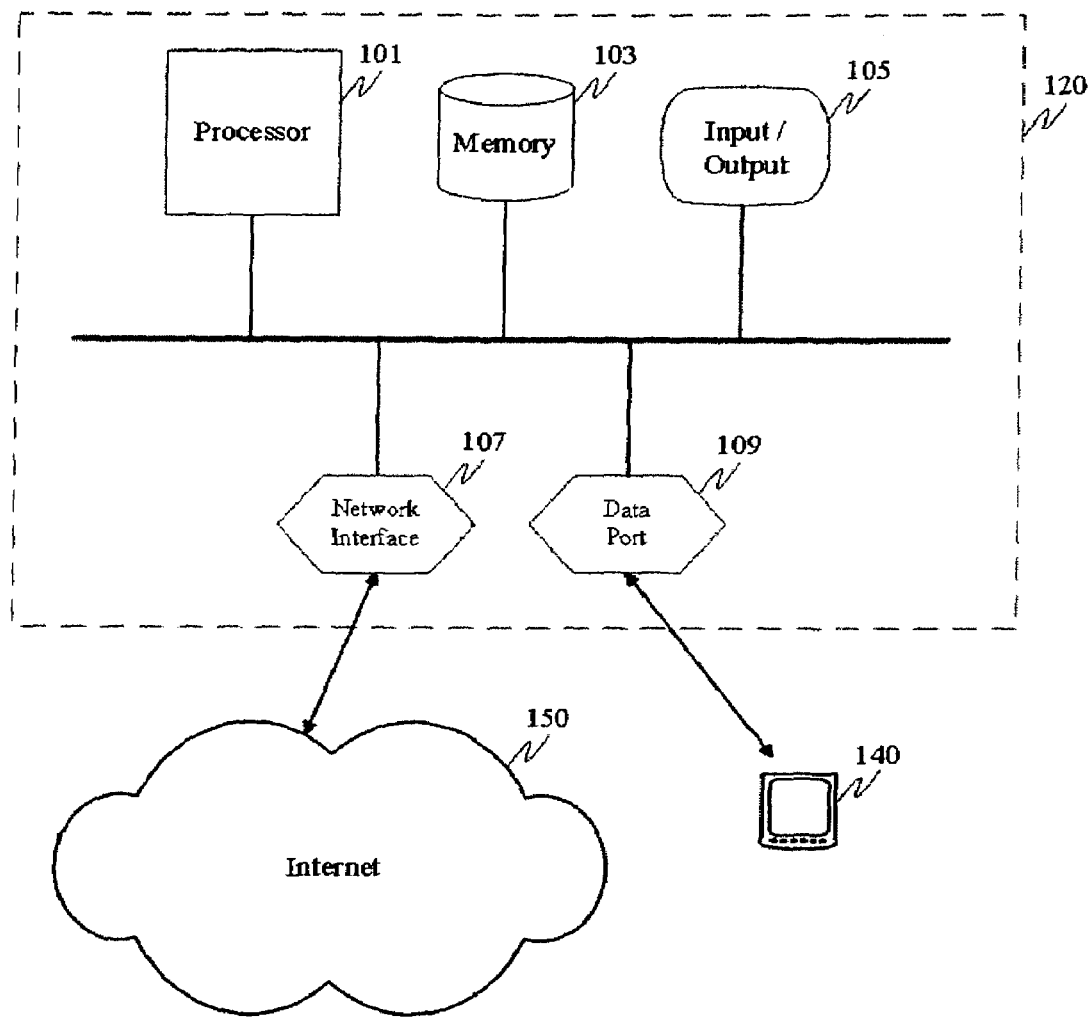
FIG. 1 depicts a system for implementing various embodiments of the invention.

FIG. 1 depicts a system 100 for implementing various embodiments of the invention. The system 100 typically includes a processor 101 containing circuitry or other logic capable of performing or controlling the processes and activities involved in the embodiments disclosed herein. The processor 101 may be a microprocessor, a combination of two or more distributed processors, an application specific integrated circuit (ASIC), or other circuitry capable of carrying out commands or instructions such as those of a computer program. For example, in some embodiments the processor 101 may run a computer program which implements a nutrition-related scheme for achieving a goal such as weight loss. Various embodiments described herein involve diet programs for achieving a goal such as losing weight or increasing the user's intake of a particular nutrient. The processor 101 is configured to communicate with a memory 103, for example, via a buss 111 or other communication link.

Figure 2:
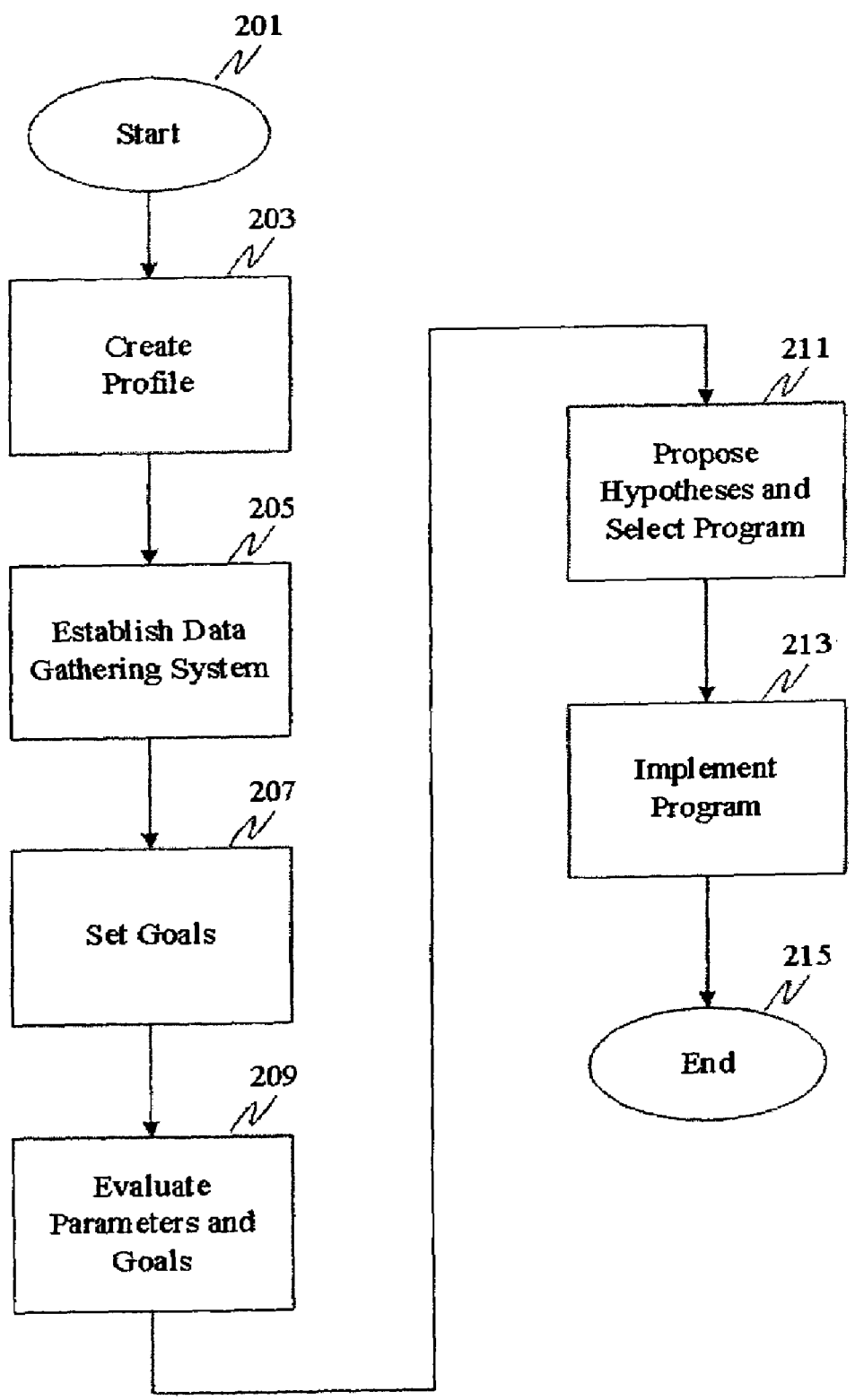
FIG. 2 is a flowchart for a method of establishing a nutrition-related scheme for achieving a goal in accordance with various embodiments of the invention.
Figure 3:
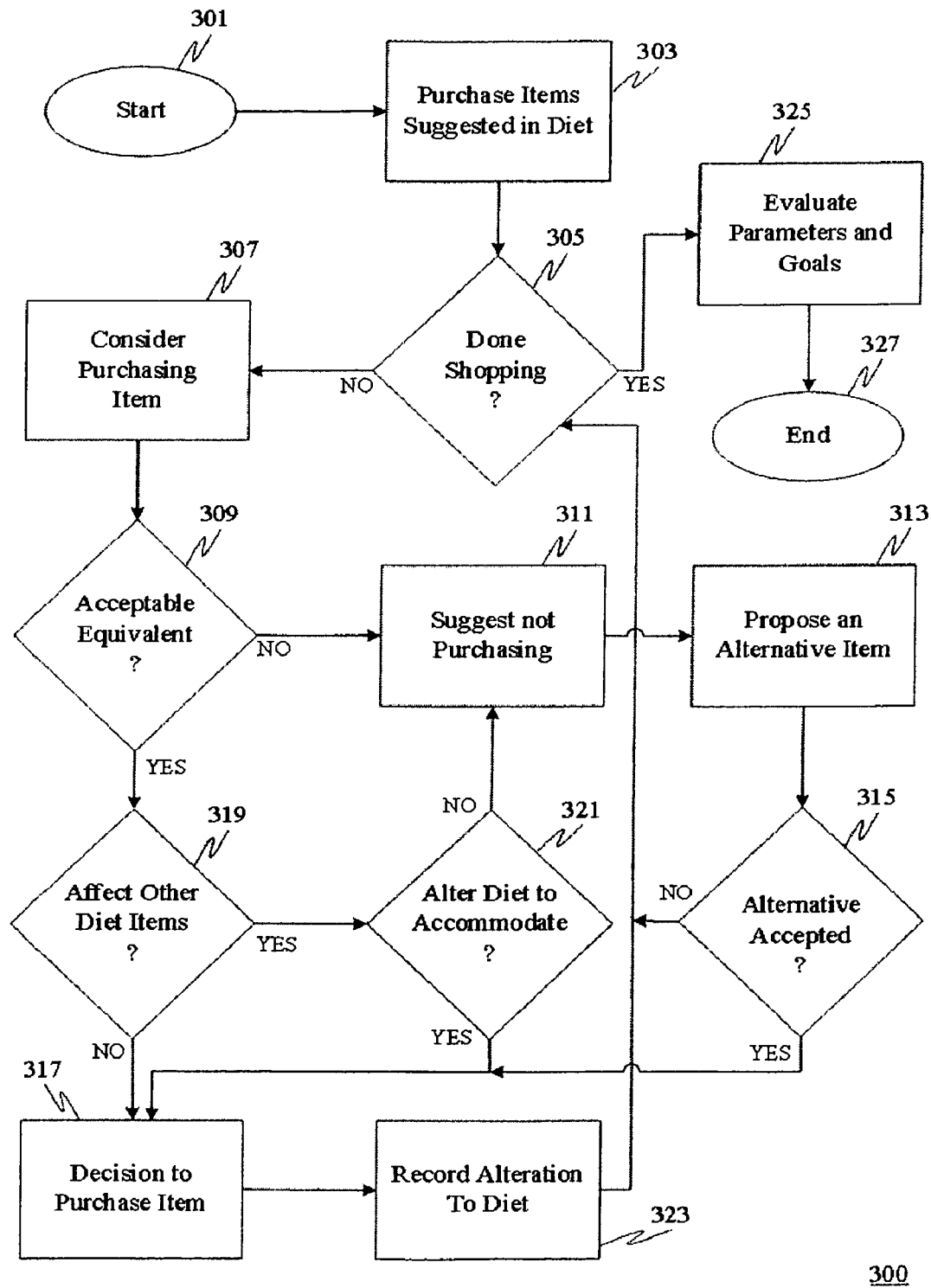
FIG. 3 is a flowchart for a method of purchasing food according to various embodiments of the invention.

The memory 103 may be any of several types of storage devices used for storing computer programs, routines, or data, including instructions and data for carrying out activities of the various embodiments such as the activities discussed in conjunction with FIGS. 2 and 3. The memory is generally used to store a computer program and associated data for implementing a nutrition-related scheme such as a pre-planned diet. The memory 103 may be embodied in any of several different forms, for example, as random access memory (RAM), read only memory (ROM), flash memory, registers, hard disk, or removable media such as a magnetic or optical disk, or other storage medium known in the art. The memory 103 may comprise a combination of one or more of any of these storage devices.

The system 100 also includes one or more input/output (I/O) devices 105. Depending upon the specifics of the implementation, and the particular requirements of the user, the I/O devices 104 may include a computer monitor or screen, a keyboard and mouse, a tablet surface and pen, a bar code reader, a scanner, or other like types of input/output devices.

In some embodiments the processor 101, memory 103, and input/output device 105, connected by one or more busses 111, may take the form of a personal computer 120 (shown by the dotted line) or other computing or communication device such as a personal digital assistant (PDA). In some embodiments the computer 120 is operated by the user. In such embodiments it may be more convenient to the user for the computer 120 to be in the form of a PDA. In embodiments in which the primary computer 120 is a PDA there may be no need for another mobile unit 140. In other embodiments the computer 120 is operated by a merchant or consultant who assists with the diet program. In such embodiments there is typically a computer 120 and also a mobile unit 140, for example, a PDA. In some embodiments, one or more of the components 101–109 may be distributed or may be separate from the rest. For example, some embodiments may use a stand-alone bar code reader as part of the I/O device 105. The bar code reader may be separate from the computer 120, but configured to download data or be linked wirelessly.

In some embodiments the system 100 comprises a mobile unit 140 which may take the form of a PDA, a laptop computer, a tablet computer, a cellular telephone, or other like portable communication or computation device. Users often find it convenient to have mobile unit 140 for entering data and accessing information about the diet programs at the time they are making food purchase decisions, e.g., at the grocery store. Typically the mobile unit 140 is capable of downloading or uploading data from/to the computer 120 via a data port 109. In some embodiments the computer program which implements the diet program may be stored in the mobile unit 140 itself, with no need for computer 120. The mobile unit 140 may be connected to the Internet 150 or to a communication system such as a cellular telephone network.

The computer 120 also has a network interface 107 for connecting to the Internet 150. Various embodiments may be implemented by providing data to the user via the Internet, for instance, by having the user log on to an Internet website or portal. Such data may include nutritional information for various food items and various diet programs which are available. The user may also be provided such data from another existing database or data files which are not part of the Internet.

FIG. 2 depicts a flowchart 200 of activities for establishing a nutrition-related scheme for achieving a goal such as weight loss. The various embodiments involve systems and methods for achieving a common goal or combination of goals, for example, a dietary objective such as losing weight or increasing the intake of a particular nutrient. The flowchart of FIG. 2 illustrates a pre-planned weigh loss diet as an exemplary nutrition-related scheme. However, weight loss through a controlled diet is but one of many different goals which may be achieved. The various embodiments disclosed herein may be tailored to meet other nutrition-related goals, and well-being or health-related goals as well. In addition to weight loss dieting, examples of nutrition-related goals include increasing or decreasing one or more particular nutrients in a diet, decreasing undesirable food products in a diet, increasing/decreasing the intake of a nutrient during a certain part of the day, or the like. Examples of well-being related goals include strength and/or stamina training, muscle building, general exercise and physical conditioning, increasing one's flexibility, or the like. Methods and systems according to various embodiments may be practiced by combining together any number of these goals, or other such goals, in an effort to achieve a primary goal (e.g., exercise and dieting to achieve weight loss).

The method depicted in FIG. 2 pertains to the creation of a nutrition-related scheme. The method begins at 201 and proceeds to 203 for the creation of a user profile. Depending upon the goal to be achieved or the level of effort to be applied, the creation of a user profile may be a fairly basic process or may entail significantly more data gathering, measurement and recording. At one end of the spectrum, the creation of a user profile may be as straightforward as recording a handful of relevant parameters, for example, the user's weight, age, gender, and possibly an estimated level of physical activity. On the other hand, a more intensive effort may involve gathering, measuring and recording a great deal more information concerning the user's physical parameters. This detailed information may include parameters such as: the user's food preferences, previous food intake and habits, allergies, history of weight gain, physical conditioning, physical impairments, strength and flexibility, heart rate at rest, heart rate during exertion, time available for exercise, the user's work schedule, the amount of physical activity involved in the user's job, medical conditions, prescription drugs being taken, whether the user personally prepares their own meals, how often the user eats out at restaurants, whether the user does the shopping and makes buying decisions, the types and variety of food available at local grocery stores, budgetary constraints, or any number of other like types of data which may have an affect on the user's goals.

Typically, a computer program takes these parameters as input, and generates an individualized customer profile which may then be used in generating a shopping list consistent with a nutrition-related scheme. The computer program which generates an individualized customer profile may run on a computer 120 which may either be under control of the user, or under control of another who is responsible for running the diet programs, like a merchant specializing in such activities. In one embodiment, the customer profile is transmitted to a user's mobile unit 140 (e.g., PDA), which may be used when shopping at a supermarket. Once the user profile has been created the method proceeds to 207

Block 207 pertains to the type of data gathering, scheduling, and intermediate goal measurement to be used in implementing the program. The effectiveness of these activities—data gathering, scheduling, and intermediate goal measurement—often have a direct bearing on the chances of successfully achieving a goal. Data is preferably recorded for each food item at the time it is purchased, and again when it is consumed. The particular types of data which are stored for each food item include, for example, calories, fat content, size/weight of item, number of items purchased, date of purchase, date of consumption, cost of the item, or the like. A simple, but effective approach may be achieved by using pen and paper to enter the user's data. This approach, however, tends to be time consuming and generally requires that the data be transposed into a more usable format at some juncture. Users may find it easier to enter details of each purchased food item into a PDA, or use a bar code reader, an optical character recognition scanner, or an RFID detector, in order to have the data stored in an electronic format. The complete nutritional details for recurring food purchases need only be entered once, when a new food item is initially purchased for the first time. By doing this over time, a database of the detailed nutritional data for the user's food preferences will eventually be populated. After an initial purchase and data entry for an item, subsequent purchases of the item will entail only entering the quantity being purchased. The nutritional data and other details can be retrieved from previous entries or preexisting portions of the database. The user may also log on to an Internet website, or use an established database or other type of preexisting data, and simply select the items (or types of items) which were purchased/consumed or are being considered for purchase or consumption. The website or database may have available a complete set of data for a variety of items, so the user only needs to indicate the selection in order to capture the nutritional data for a given quantity being purchased of any of the variety of pre-stored items.

The data for the user's purchases, consumption and exercise activities do not necessarily need to be gathered in the same manner at the initial point of entry. It is sometimes more convenient, and thus more effective, to record data in one manner and then transform the data at a later time to the format required for the computer program or other logic used to implement the nutrition-related scheme. For instance, it may be awkward to enter data into a PDA during a meal being eaten in a restaurant. Yet it is important for the sake of accuracy and completeness to record data for the meal in a timely manner, rather than trying to remember what was eaten much later after the fact. It may be more effective to use a handheld tape recorder, the voice recording function of a cellular telephone, or an image scanner for restaurant menu items, and then later transpose the data into a useable format. Similar means of data gathering may be used to record the user's exercise and physical activities, or food purchases. The data, whether it is entered into a PDA or captured as image or voice recordings, may be transposed and provided to, or reentered at a main computing point such as a desktop computer 120 or a web-based location 150. Once the data gathering and recording systems have been decided upon in 205 the method proceeds to 207.

In 207 the goals are set for the nutrient-related scheme or pre-planned diet program. The primary goal may be to lose a certain amount of weight, to fit into a particular size of clothing, to gain a predefined amount of strength, or to attain any other measurable, physical parameter. Once the primary goal and schedule have been set, it may be useful to set some intermediate goals in order to gauge the progress of the scheme. For example, a person weighing 220 pounds may have a goal of losing forty pounds in a four month period, averaging ten pounds lost per month. However, weight loss does not always occur in a perfectly linear manner. It is sometimes easiest to shed the first few pounds when going on a diet, than it is to lose the last few pounds towards achieving a goal. Hence, the intermediate goals may be adjusted in a nonlinear fashion. Forty pounds of weight loss in four months may be scheduled as twelve pounds lost in the first month, followed by a ten pound loss the next month, and two months of nine pound losses, respectively.

The intermediate goals of 207 may take a form other than that of the primary goal. If the goal is weight loss, the intermediate goals may involve a predetermined maximum caloric intake (e.g., 1,200 calories per day), or a certain amount of physical activity (e.g., walking three miles per day, or burning 1,000 calories on a treadmill). A number of intermediate goals may be specified, possibly having different scheduled measurement periods. For example, a diet/exercise regimen may involve 1,200 calories per day, three miles of walking per day, coupled with a weekly weigh-in associated with intermediate weight goals. Once the goals have been set in 207 the method proceeds to 209.

In 209 it is determined whether the primary goal and intermediate goals are reasonable. For example, except in cases of extreme obesity, it is generally considered unreasonable for a person to lose an excessive percent of their body weight, say, more than forty percent (or some other predetermined percent). In addition to determining whether the primary goal itself is reasonable, block 209 is also concerned with determining whether the time period for attaining the goal (if any is specified) is reasonable. It may be unreasonable, or unhealthy, to lose a reasonable amount of weight (e.g., 15% of body weight) within an inordinately short period of time through ordinary dietary means—that is, without a surgical procedure such as stomach stapling. For instance, it may be ill advised for a person weighing 220 pounds to set a goal of losing 40 pounds within a month. Once the goals have been set in 207 and determined to be reasonable in 209 the method proceeds to 211.

In 211 a list is generated which includes one or more hypothetical diet programs which may be suitable for attaining the primary goal. The generation of the list of hypothetical diet programs may entail the creation of one or more specially tailored diet programs, each plan being designed to accommodate the user profile. The list may also, or alternatively, include a number of established diets. Examples of established diets include the Atkins Diet™, South Beach Diet™, Scarsdale Diet, Carbohydrate Addicts Diet™, Sacred Heart Diet, Hills Prescription diet™, Mediterranean diet, or the like. Other established diets include the fiber diet, fat flush diet, grapefruit diet, cabbage soup diet, apple cider diet, macrobiotic diet, vegetarian diet, sugar free diet, healthy heart diet, raw food diet, diabetic diet, high blood pressure diet, arthritis diet, low salt diet, low protein diet, zone diet, bodybuilding diet, 1000 calorie diet, or other like diets. Once a list of hypothesis diets has been established, the diet programs are evaluated for feasibility based on the user's profile. The list is then winnowed down to include only those deemed feasible and calculated to have the best chance of succeeding in attaining the primary goal. It is sometimes the case that the list will include several hypothetical diet programs which appear equally likely to succeed, since it may be difficult to determine which, if any, is more suitable for a particular user. If more than one hypothetical diet program is generated the user may be given a choice among the alternative programs deemed equally likely to succeed. Allowing the user to choose may be advantageous in that it allows selection of the program which the user feels is most suitable for their personal habits, propensities and preferences.

The overall nutrition-related scheme constructed to achieve the goal (e.g., weight loss) may entail several combined efforts towards achieving the goal. For example, a controlled diet may be combined with an exercise regimen which complements the diet. The exercise regimen may be constructed in much the same manner as the diet, as described above. That is, a list can be generated which includes one or more specially tailored exercise programs in combination with a number of established programs. One criterion in choosing an exercise regimen is whether it complements the diet of the user. For example, an exercise regimen may be purposefully scheduled to burn away the calories of the day's largest planned meal in accordance with the diet. Once the list has been evaluated for feasibility and winnowed down, the user may be given a choice from among the alternative exercise programs remaining on the list.

Upon selecting a hypothesis scheme in 211 the method proceeds to 213. In 213 the nutrition-related scheme is implemented. In carrying out the scheme, it may be determined through measurement and progress monitoring that adjustments to the nutrition-related scheme are needed to accommodate food items which conflict with the dietary scheme. Details for implementing the program, including making mid-stream adjustments, if warranted, are illustrated in the flowchart of FIG. 3 and discussed in the following paragraphs. Following implementation of the scheme in 213 the method proceeds to 215 and ends.

FIG. 3 is a flowchart 300 of activities for purchasing food in a nutrition-related scheme in accordance with various embodiments. Quite often, if a person strictly adheres to a well planned diet, it is likely the diet will ultimately succeed. Problems arise, however, when people deviate from the diet, substituting different types or quantities of food which deviate from the food items in the dietary scheme. Sometimes food items are substituted by the user due to unavailability of the diet items. At other times, the dieter simply craves food items which are inconsistent with the diet. Quite often a substituted item by itself may not seem likely to be inconsistent with the diet, but when combined with other food items the may pose a problem. That is, a substituted food item may interact with one of the approved dietary food items in a negative manner. It is useful for the user to know whether a substituted item is harmful to the diet, and if so, whether other aspects of the diet may be compensated to make up for the substituted item. The method depicted in FIG. 3 solves these problems.

The method begins in 301 and proceeds to 303 where the user purchases one or more items suggested by the system which are known to be consistent with the nutrition-related scheme. If the user purchases only known and approved items in accordance with block 303, sticking with the diet will be very straightforward. However, it is when the user deviates from the list of approved diet items that the likelihood of attaining the primary goal is in jeopardy. The method proceeds to 305 where it is determined whether the user is done shopping. If no more items are to be purchased the method proceeds along the "YES" branch from 305 to 325 for incorporation of the data pertaining to the purchased items. However, if it is determined in 305 that there is more shopping to be done, the method proceeds along the "NO" branch to 307.

In 307 the user considers purchasing a new item which has not yet been approved in accordance with the nutrition-related scheme. The new item being considered in 307 is assumed to be an item which has not, up to this point, been a part of the diet program since items within the diet program were purchased in block 303. The new item may be a food product which caught the user's eye while shopping. It may be the case that the item is equivalent to an approved item, but is simply a different brand which has not yet been entered into the database. Or the item may be a variant of a previously purchased item, for instance, whole milk is being considered rather than 2% milk which was purchased in the past. The present method will determine whether the new item being considered, a proposed substitute item, is acceptable for the diet or not.

The method proceeds from 307 to 309 where it is determined whether or not the new item is equivalent to an approved diet item, in which case it may simply be substituted for the approved item. As the user selects items to place in the shopping cart in 307, the user profile and nutrition-related scheme are applied against the placed item, and an indicator may be presented to the user to signify how appropriate the item is in relation to the customer profile. Typically, a program in the mobile device 140 applies the customer profile or nutrition-related scheme against any one of, or combination of, the items that are placed in the shopping cart and being considered for purchase. A message may be displayed to signify how conducive the selected item is in helping the user achieve the stated goal. If the new proposed substitute item is not an acceptable equivalent to an approved diet item the method proceeds along the "NO" branch to 311. In 311 the program suggests to the user to forego purchasing the new item. It is anticipated that the user will generally abide by block 311 and opt to not purchase unacceptable items. However, if the user decides to purchase the new item anyway, the data for the unacceptable item is stored in the database in order to calculate its impact on the diet. If a purchased item is not conducive to the stated goal, the user profile and nutrition-related scheme may be adjusted accordingly, taking that item into consideration, such that the stated goal is still maintained when making the next selection. From 311 the method proceeds to 313 where the system suggests an acceptable alternative item which may be purchased in lieu of the unacceptable new item. The suggestion of an alternative item is done to satisfy the user, while at the same time staying within the guidelines of the diet program. The system may propose a list of several alternative items from which the user may choose.

The suggested alternative, or list of alternatives, are generated by the system based on its database of food items or access to a similar remote database. For example, the user's PDA may access a food item database maintained by the store, thus, coming up with a list of one or more acceptable alternatives which are known to be available during the present shopping trip. The suggested alternatives may be of a similar type of food as compared to the unacceptable item which had been considered for purchase by the user. Consider, for example, the suggestions for potato chips which the system determined to be unacceptable to the diet. In place of potato chips the system may suggest pretzels as an acceptable alternative food since pretzels are similar to potato chips. The system may also propose alternate items which are a different type of food than the unacceptable item, but are known to be consumed in a similar manner or context. For example, in place of potato chips the system may suggest purchasing popcorn, a snack item which differs from potato chips but may possibly work as a substitute since it may also be consumed as a snack food in a manner similar to potato chips.

Once the acceptable alternate food items have been proposed to the user in 313 the method proceeds to 315 to determine which, if any, of the alternatives the user selects. If no alternative is found to be acceptable to the user the method proceeds along the "NO" branch from 315, looping back to 305 to determine whether there is any more shopping to be done. On the other hand, if the user decides in 315 to purchase one of the acceptable alternatives proposed by the system the method proceeds along the "YES" branch to 317.

Back in 309 if the item is determined to be an acceptable equivalent to an approved diet item, the method proceeds along the "YES" branch to 319 where it is determined whether the item negatively interacts with one or more other items in the diet. In some instances an item may be found to negatively interact with other items in the diet by exceeding a nutritional budget, while in other instances an item may negatively impact the body's capacity to metabolize a predefined nutrient. For some people it would be healthier to alter the intake of a predefined nutrient, either by increasing or decreasing the amount ingested. For example, a user with a calcium deficiency may be on a diet in which the primary goal is to increase calcium intake by a specified amount. If one of the approved diet items is calcium fortified milk, the selection of tea bags in 307 as an item proposed to be purchased will negatively affect the diet since tea temporarily reduces the body's capacity to absorb calcium. In such an instance the method will proceed from 319 along the "YES" branch to 321 since tea bags affect the diet's primary goal in this example of increasing calcium intake. In 321 it is determined whether the diet may be altered in a manner acceptable to the user while still meeting the diet objectives. This may entail sending a warning: "Drinking tea within one hour of drinking milk will temporarily inhibit your body's capacity to metabolize the milk's calcium." In some instances the solution may be to suggest reducing the intake of the offending item: "Do not drink more than one-fourth cup of tea within an hour of drinking milk."

It may be the case that new food items negatively interact with the approved diet items specified in weight-loss diet programs with goals other than altering the intake of particular nutrients. For example, foods which trigger the release of insulin in the body negatively interact with the intake of high-fat content, low carbohydrate food items which are the basis of low carbohydrate (low carb) diets. Low carb diets are based on the premise that excess body fat is built up due to the body's insulin response. Insulin, a hormone produced by the body, controls the blood sugar level, triggering cells to convert carbohydrates into glucose. Insulin causes some of this converted sugar to be stored as fat if it is not used to fuel the body, and tends to keep stored fat from being burned. A low-carbohydrate diet results in less insulin being released and the body will begin to burn its own fat as fuel. By reducing the intake of carbohydrates and high-sugar-content foods, low carb diets such as the Atkins diet™ causes the body to burn fat rather than accumulating it, resulting in weight loss. Thus, if a user on a low carb diet proposes to purchase a food item which is high in carbohydrates, the proposed item may negatively interact with other food items approved for the low carb diet by exceeding a nutrient budget for carbohydrates. In such a case the method will proceed from 319 along the "YES" branch to 321 since the purchase of the proposed high carb item would counteract the effect of the approved items which are low in carb/high protein diet items. The proposed high-carbohydrate item may negatively interact with other items in the diet by exceeding the daily nutritional budget for carbohydrate intake.

Continuing with the previous example concerning tea bags and milk, if a user avoids drinking tea for at least an hour prior to drinking the calcium enriched milk, the body's capacity to absorb calcium will not be reduced. It may be the case, in 321, that the suggested dietary alteration is not acceptable to the user. For instance, maybe the user plans to drink milk during breakfast and only enjoys tea at breakfast as well. Hence, the user is not willing to wait an hour after consuming tea to drink the calcium enriched milk. In such situations it sometimes occurs that the approved diet item (milk, in this instance) may be replaced or compensated for, instead of giving up tea for breakfast. For example, in lieu of giving up tea, the system may suggest taking a time release calcium tablet in the morning—or simply drinking milk for supper instead of breakfast. However, if no such option is available and if it is determined that the suggested alteration to the user's dietary habits is not acceptable to the user, then the method proceeds along the "NO" branch to 311 and the program suggests to forgo purchasing the tea since it will adversely affect the diet.

Back in 321, if the suggested alteration to the user's dietary habits is acceptable to the user—that is, if the user agrees to delay drinking milk for at least an hour after having tea—then the method proceeds along the "YES" branch to 317. The decision to purchase the item is made in 317, and the method proceeds to block 323 for recording the data or instructions pertaining to the dietary change. Once the dietary alteration has been recorded in 323 the method loops back to 305 where it is determined whether the shopping excursion is completed.

In 305 if it is determined that all shopping at the store has been completed the method proceeds along the "YES" branch from 305 to 325 where the data pertaining to the purchased items is recorded and incorporated into the diet program. This may entail compiling a schedule of proposed meals and showing the quantities to be consumed for food items which are being purchased along with any quantities which are still available at the user's home pantry, or the user's workplace if food is consumed there. By depicting the user's pantry inventory (including the items presently being purchased) parsed into a proposed schedule of meals, the diet program can indicate to the user which items will run in short supply the soonest. Once the data from the present shopping trip has been incorporated into the database the method proceeds to 327 where it ends.

Those of ordinary skill in the art understand that data, information and signals may be represented in a number of different ways, using a variety of technologies and techniques. The logical blocks in the flow charts, circuits, and components described in connection with the various embodiments may be implemented as hardware, software, firmware, or some combination thereof. Those of ordinary skill in the art would know to implement the described embodiments using various designs options, depending upon the particular constraints and considerations of the situation. Such design choices are not a departure from the scope of the present invention.

The various logical blocks depicted in the flow charts, circuits, and components may be implemented using a personal computer, a microprocessor, a controller, a digital signal processor (DSP), an application specific integrated circuit (ASIC), using discrete or integrated circuitry, or a combination of these. A general purpose processor may be a microprocessor, but in the alternative, the processor may be any conventional processor, microcontroller, or state machine.

The various steps and activities in the embodiments described herein may be performed in the exemplary order illustrated in the figures, or another order, depending upon the particularities of the implementation. For example, the block 323 in FIG. 3, recording an alteration to the diet, may be performed in the order depicted in the figure, or it may be performed immediately ahead of or behind block 325, depending upon the particular implementation of the embodiment. Various other activities and steps may be performed in a sequence other than that illustrated in the figures.

The disclosure of the various embodiments is provided so as to enable those of ordinary skill in the art to make and use the present invention. Design choices and modifications to the various embodiments will occur to practitioners of ordinary skill in the art without departing from the spirit or scope of the invention. The present invention is not intended to be limited only to those specific versions which are discussed herein for the sake of illustration, but is to be accorded the widest scope for the features and aspects of the invention enabled herein.

What is claimed is:

1. A method of evaluating proposed food purchases comprising:
   storing a nutrition-related scheme based on achieving a primary goal, the nutrition-related scheme including a list of approved food items;
   receiving an input regarding acceptability of a proposed substitute item which is not one of the approved food items;
   making a determination of whether the proposed substitute item would negatively interact with any of the approved food items; and communicating, based on the determination, whether the proposed substitute item would negatively interact with at least one of the approved food items.

2. The method as described in claim 1, wherein the proposed substitute item would negatively interact with the at least one of the approved food items by affecting a user's ability to metabolize the at least one of the approved food items.

3. The method as described in claim 2, wherein the primary goal of the nutrition-related scheme is to alter the user's intake of a predefined nutrient.

4. The method as described in claim 1, further comprising:
generating a shopping list based on the nutrition-related scheme comprising one or more of the approved food items.

5. The method as described in claim 1, further comprising:
developing the nutrition-related scheme based on a profile of a user, the profile comprising a number of parameters;
wherein one of the number of parameters is the user's weight.

6. The method as described in claim 1, wherein the nutrition-related scheme includes a schedule for consuming at least portions of the approved food items.

7. The method as described in claim 1, wherein the proposed substitute item would negatively interact with the at least one of the approved food items by affecting said at least one of the approved food items' ability to be metabolized.

8. A computer readable media embodying a method of evaluating proposed food purchases, the method comprising:
storing a nutrition-related scheme based on achieving a primary goal, the nutrition-related scheme including a list of approved food items;
receiving an input from regarding acceptability of a proposed substitute item which is not one of the approved food items;
making a determination of whether the proposed substitute item would negatively interact with any of the approved food items; and
communicating, based on the determination, whether the proposed substitute item would negatively interact with at least one of the approved food items.

9. The computer readable media as described in claim 8, wherein the primary goal of the nutrition-related scheme is to alter the user's intake of a predefined nutrient.

10. The computer readable media as described in claim 8, further comprising:
generating a shopping list based on the nutrition-related scheme comprising one or more of the approved food items.

11. The computer readable media as described in claim 8, further comprising:
developing the nutrition-related scheme based on a profile of a user, the profile comprising a number of parameters for the user including the user's weight.

12. The computer readable media as described in claim 8, wherein the nutrition-related scheme includes a schedule for consuming at least portions of the approved food items.

13. The computer readable media as described in claim 8, wherein the proposed substitute item would negatively interact with the at least one of the approved food items by affecting said at least one of the approved food items' ability to be metabolized.

14. A system for evaluating proposed food purchases comprising:
a memory configured to store a nutrition-related scheme based on achieving a primary goal, the nutrition-related scheme including a list of approved food items;
an input unit configured to receive an input regarding acceptability of a proposed substitute item which is not one of the approved food items;
a processor configured to run a program for making a determination of whether the proposed substitute item would negatively interact with any of the approved food items; and
an output unit configured to communicate whether the proposed substitute item would negatively interact with at least one of the approved food items based on the determination.

15. The system as described in claim 14 wherein the input unit is a keyboard and the output unit is a screen.

16. The system as described in claim 14 wherein the processor is part of a PDA.

17. The system as described in claim 14, further comprising:
a bar code scanner;
wherein the barcode scanner forms at least part of the input unit.

18. The system as described in claim 14, wherein the primary goal of the nutrition-related scheme is to alter a user's intake of a predefined nutrient.

19. The system as described in claim 14, wherein the proposed substitute item would negatively interact with the at least one of the approved food items by affecting said at least one of the approved food items' ability to be metabolized.

* * * * *